United States Patent [19]

Console et al.

[11] 4,145,291
[45] Mar. 20, 1979

[54] DISINFECTING MEANS WITHIN A WATER DISPENSER

[75] Inventors: Ortha M. Console, Glendale; Alvah M. Griffin, Torrance, both of Calif.

[73] Assignee: Foremost-McKesson, Inc., San Francisco, Calif.

[21] Appl. No.: 831,262

[22] Filed: Sep. 7, 1977

Related U.S. Application Data

[63] Continuation of Ser. No. 726,762, Jun. 27, 1976, abandoned.

[51] Int. Cl.² ............................ C02B 3/10; B67D 3/00
[52] U.S. Cl. ............................ 210/232; 210/466; 210/474; 210/479; 210/501; 222/181; 222/189
[58] Field of Search .............. 210/198 R, 232, 234, 210/238, 64, 501, 466, 474, 479; 21/58, 91; 222/181, 457, 189

[56] References Cited

U.S. PATENT DOCUMENTS

| | | | |
|---|---|---|---|
| 310,130 | 12/1884 | Frank ........................... | 21/58 |
| 680,384 | 8/1901 | Kingzett ........................ | 21/58 |
| 730,612 | 6/1903 | Conover ........................ | 222/181 |
| 959,111 | 5/1910 | Buckland ....................... | 21/58 |
| 1,228,836 | 6/1917 | Schulse ......................... | 222/457 |
| 1,473,331 | 11/1923 | Bechhold ....................... | 210/64 |
| 1,557,234 | 10/1925 | Bechhold ....................... | 210/501 |
| 1,935,136 | 11/1933 | Thibert .......................... | 210/234 |
| 2,283,883 | 5/1942 | Conconi ......................... | 210/501 |
| 2,508,602 | 5/1950 | Gotz .............................. | 210/64 |
| 2,904,857 | 9/1959 | Gotz .............................. | 21/58 |
| 3,327,859 | 6/1967 | Pall ................................ | 210/501 |
| 3,372,808 | 3/1968 | Sebo .............................. | 210/501 |
| 3,408,295 | 10/1968 | Vaichulis ........................ | 210/198 R |
| 3,618,828 | 11/1971 | Schinella ........................ | 222/457 |
| 3,872,013 | 3/1975 | Nishino .......................... | 210/501 |
| 3,923,662 | 12/1975 | O'Brien .......................... | 210/175 |
| 3,980,563 | 9/1976 | Greutert ......................... | 210/232 |
| 4,024,991 | 5/1977 | Tyson et al. .................... | 210/501 |

FOREIGN PATENT DOCUMENTS

| | | | |
|---|---|---|---|
| 384547 | 5/1932 | United Kingdom ............... | 210/501 |
| 662662 | 12/1951 | United Kingdom ............... | 210/36 |

*Primary Examiner*—Thomas G. Wyse
*Assistant Examiner*—Ernest G. Therkorn
*Attorney, Agent, or Firm*—Flehr, Hohbach, Test, Albritton & Herbert

[57] ABSTRACT

Apparatus for disinfection of drinking water where the water is stored in a tank or other container from which it is dispensed. The invention is characterized by use of a porous ceramic body having metallic silver dispersed within the same and which is immersed in the water. Silver ion is released from the absorbed liquid of the body at a controlled level of concentration to inhibit the growth of organisms.

1 Claim, 5 Drawing Figures

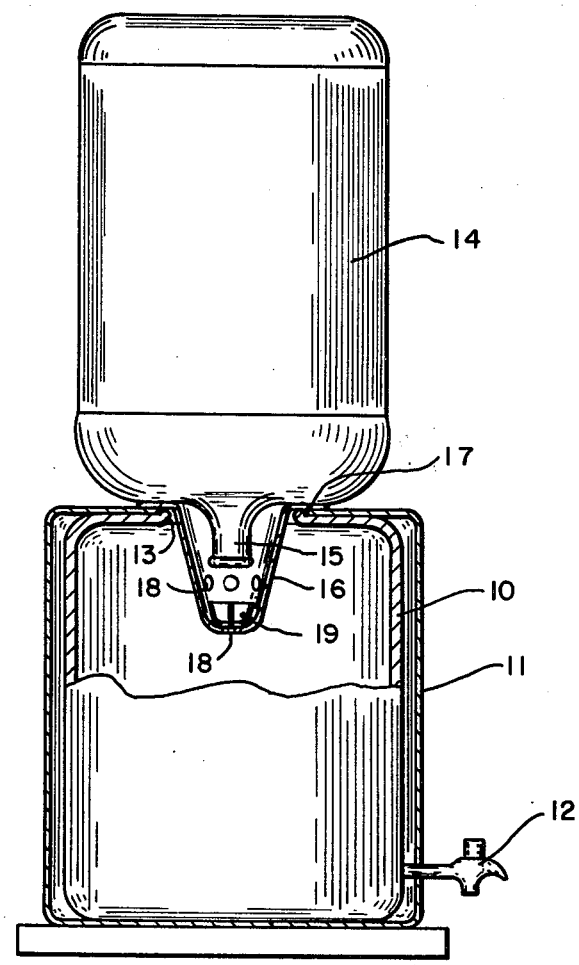
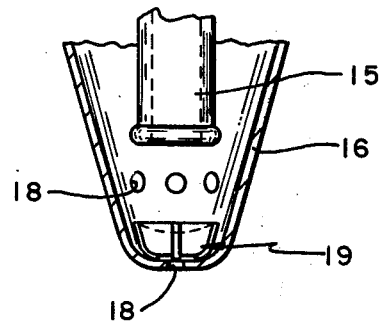
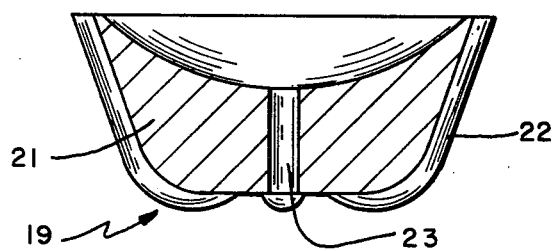
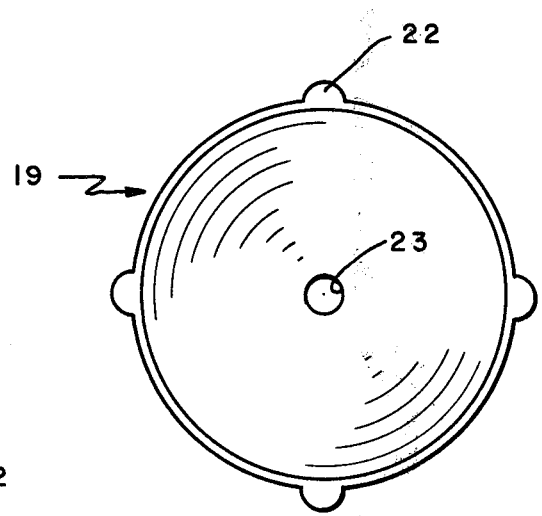
FIG.—1
FIG.—2
FIG.—3
FIG.—4

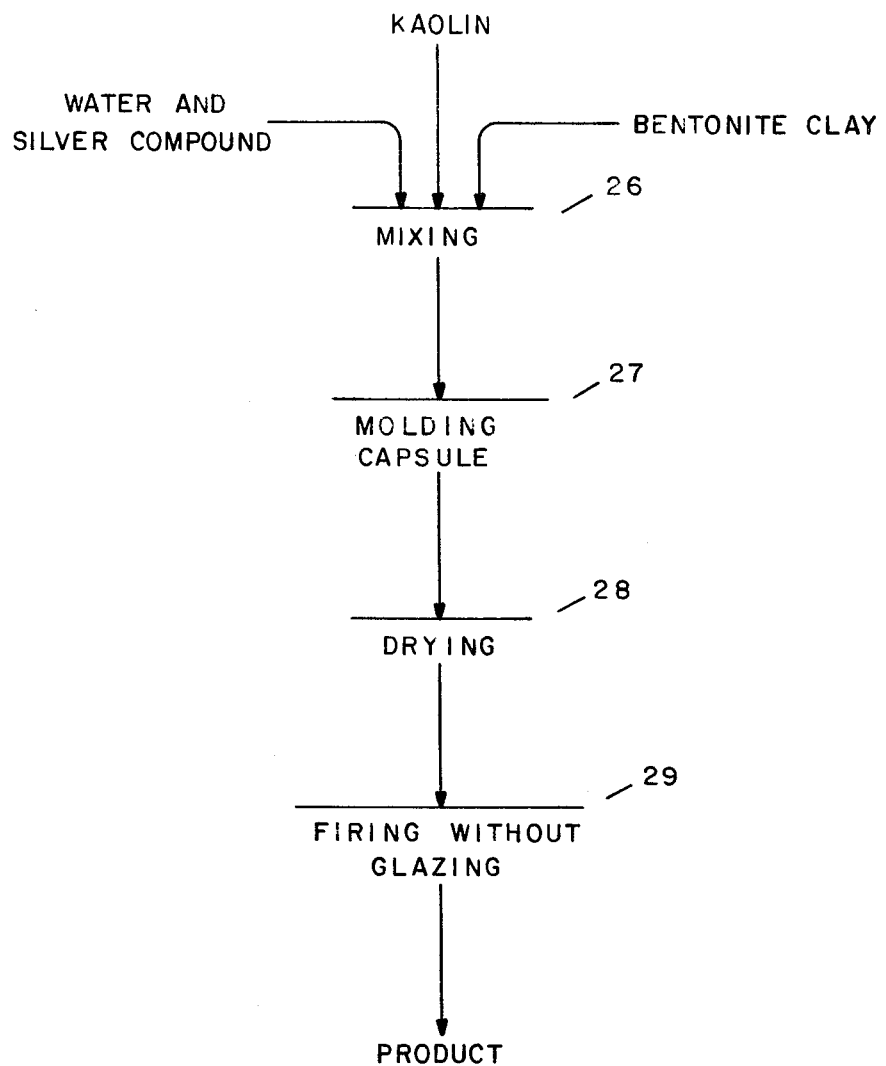
FIG.— 5

DISINFECTING MEANS WITHIN A WATER DISPENSER

This is a continuation, of application Ser. No. 726,762, filed June 27, 1976, now abandoned.

BACKGROUND OF THE INVENTION

The present invention relates generally to the disinfecting of drinking water by use of apparatus making use of silver ion as a disinfecting agent.

It has been known that silver ion has a disinfecting effect upon organisms commonly found in drinking water. However, simple apparatus and methods making use of silver ion and applicable to drinking water dispensers, have not been generally available. This is attributed to inability of prior apparatus and methods to maintain an effective silver ion concentration over extended periods of time, cost of the apparatus or devices required, the nature of the apparatus and devices which have required changes in conventional dispensers, and inability to control the ion concentration between desired levels. Among the apparatus and devices employed for making use of silver ion for water disinfection, reference can be made to filters having porous filter mediums (e.g., ceramic or carbon) containing metallic silver, electrolytic cells for generating and introducing silver ion into water flowing through the cell, and silver-plated or silver-containing coatings on bodies in contact with the water. Such apparatus and devices have not provided simple means applicable to conventional water dispensers capable of developing and maintaining a silver ion concentration to an effective level for disinfection.

SUMMARY OF THE INVENTION AND OBJECTS

In general it is an object of the present invention to provide a simple apparatus capable of disinfecting and maintaining drinking water in a safe condition in dispensing equipment.

Another object is to provide a device in the form of a capsule which when introduced into a tank or reservoir containing drinking water serves to effect disinfection with respect to bacterial contamination, and to maintain the water in a safe condition.

Another object of the invention is to provide a device in the form of a capsule which can be introduced into conventional water dispensers, and which will effect disinfection and maintain the water in a safe condition.

Another object is to provide a water disinfecting capsule in the form of a ceramic body which contains dispersed metallic silver in such form that when the capsule is immersed in drinking water silver ion is released in a controlled manner to provide a level of silver ion concentration effective to disinfect and to maintain the water disinfected.

Another object is to provide a drinking water disinfecting apparatus which is especially adapted for use with drinking water which contains no more than about 150 parts per million dissolved solids.

In general, the present invention consists of apparatus including a capsule in the form of a body made of porous, absorbent ceramic material, the body having metallic silver dispersed therein. When the capsule is immersed in drinking water contained within a tank or container it functions to absorb and retain water therein and to effect dispersion of silver in the absorbed water. This in turn serves to maintain a level of silver ion in the body of water in the reservoir that is effective to control the growth of contaminating organisms. Also the disclosure includes a method for the manufacture of the capsule, and a method of effecting disinfecting of drinking water making use of the capsule.

Additional objects and features of the invention will appear from the following description in which the preferred embodiments have been set forth in detail in conjunction with the accompanying drawing.

BRIEF DESCRIPTION OF THE DRAWING

FIG. 1 is a side elevational unit of a conventional olla dispenser with a capsule made according to the present invention installed therein.

FIG. 2 is an enlarged detail in section illustrating a suitable positioning of the capsule within the olla dispenser.

FIG. 3 is a side elevational view illustrating a suitable form for the capsule.

FIG. 4 is a plan view of the capsule shown in FIG. 3.

FIG. 5 is a diagram illustrating steps in a method for manufacture of the capsule.

DESCRIPTION OF THE PREFERRED EMBODIMENTS

The drinking water dispenser illustrated in FIG. 1 consists of a container 10 which may be enclosed within a housing or shell 11 and may be made of suitable material, such as glass, plastic, stainless steel or ceramic. Its lower portion is in communication with the dispensing faucet 12. It has a relatively wide opening 13 in its upper end. A container 14, which generally is in the form of a bottle made of glass or suitable plastic, is inverted and supported upon the upper end of the container 10, with its neck 15 extending through the opening 13. A basket 16 also is disposed within the opening 13, and is provided with a skirt or flange 17 which is interposed between the lower end of the bottle 14 and the upper end of the container 10. The basket is generally annular in horizontal section and is provided with openings 18 through which water may pass from the interior of the basket into the container 10.

Supported within the basket and disposed beneath the lower open end of the bottle neck 15, there is a capsule 19 as shown in FIGS. 3 and 4. The capsule consists of a body 21 of porous ceramic material, made by a method as presently explained. The porosity of the body is such that when it is immersed in water, a substantial amount of water is absorbed within the pores of the body by capillarity. The functioning of the capsule is not critical with respect to its form or configuration. As illustrated the body is annular as viewed in plan. Its upper side is concave, and its lower side convex. Stated another way, it is in the form of a shallow cup, with the vertical thickness of the body increasing from the perimeter toward its central portion. The sides and lower surfaces of the body are shown provided with integral ribs 22. The purpose of these ribs is to provide a support upon the underlying surface of the basket 16, whereby spaces are provided between the body of the capsule and the adjacent surfaces of the basket to permit the free access of water. The central portion of the body is shown provided with a duct or vent 23 which serves to prevent any entrapment of air immediately above or below the body.

A desirable method for manufacturing the capsule is outlined in FIG. 5. The principal ingredient is a relatively pure form of kaolin or clay. As indicated in step 26, a sufficient amount of water and silver compound is mixed with the kaolin to form a mixture of proper moldable characteristics. To facilitate the smoothness and moldability of the mix, a small amount of clay is added of a type which swells when wetted, such as bentonite. In the mixing operation the silver solution is uniformly distributed throughout the mass. The mix is then introduced into suitable molds in step 27, such as molds capable of producing the configuration shown in FIGS. 3 and 4. The dimensions of the mold cavity are such as to produce the desired dimensions after shrinkage during subsequent treatment. The molded forms are then subjected to drying 28 to reduce the moisture content and to provide forms having sufficient strength for subsequent firing. In general, it is satisfactory to reduce the moisture content to less than 1% in step 28. The dried forms are then fired in a suitable furnace as indicated in step 29, with the temperatures and times being controlled to prevent glazing. By way of example, the total firing time may be of the order of 12 hours, including initial heating from ambient temperature up to a firing temperature of 1900° F., holding this temperature for about 2 hours, and then permitting the capsule to cool to at or near ambient temperature for an additional 12 hours. In addition to providing a capsule of sufficient structural strength for use in the manner previously described, firing to such temperatures causes reduction of the silver compound to form metallic silver, with the metallic silver being relatively uniformly dispersed in the porous ceramic body.

While adding the silver solution in step 26 is preferred it is possible to immerse the dried capsule in the silver solution after drying in step 28 to effect absorption into the interior of the body. In this event further drying is required before firing.

With respect to the composition of the kaolin or clay employed, the mix may contain 90% of a relatively pure form of kaolin, and 10% of bentonite clay. A typical analysis of such a mix is as follows:

$Al_2O_3$: 37.3%
$SiO_2$: 46.9
$Fe_2O_3$: 0.7
$CaO$: 0.06
$MgO$: 0.2
$KOH + Na_2O$: 0.4
$TiO_2$: 1.4
$SO_3$: 0.1
$P_2O_5$: 0.06
Ignition loss: 12.87

The kaolin used in preparing the above mix by itself analyzes as follows:

$Al_2O_3$: 39.21%
$SiO_2$: 44.95%
$Fe_2O_3$: 0.49%
$CaO$: 0.06%
$MgO$: 0.04%
$KOH + Na_2O$: 0.13%
$TiO_2$: 1.51%
$SO_3$: 0.01%
$P_2O_5$: 0.07%
Ignition loss: 13.57%

With respect to the silver compound employed, it is desirable to employ a compound which has good solubility in water, such as silver nitrate, silver acetate, silver chlorate, silver lactate, or silver picrate. Likewise, all of these compounds or salts are reduced at a temperature of the order of 1900° F. to provide elemental or metallic silver. Other silver salts are likewise reduced at a temperature of the order of 1900° F., but have relatively low solubility compared to the salts previously mentioned. In this connection reference can be made to such compounds or salts as silver bromate, carbonate, chromate, citrate, iodate, nitrite, oxide, perchlorate, permanganate, phosphate, selenate and sulfate. In the event such silver compounds are used they may be introduced into the mix in finely powdered form, or as a slurry.

A convenient size for a capsule having a configuration like FIGS. 3 and 4 is one having a volume of 3.66 cubic inches (60 ml) with a weight of 3.46 ounces (98 grams). When constructed in the manner described with reference to FIG. 5, the capsule will absorb about 24 grams of water. Good results are secured when such a body contains about 2.0 grams of metallic silver, which is the amount of metallic silver provided by 3.15 grams of silver nitrate added to the mix. The effectiveness of the capsule does not appear to be highly critical with respect to the amount of metallic silver in a capsule of given weight. Good results are obtained when the capsule contains an amount of metallic silver ranging from 1.5 to 3 grams of dispersed silver for a capsule weighing about 100 grams. The amount of metallic silver can be increased in proportion to an increase in the weight of the capsule.

When a capsule constructed as described above is introduced into a dispensing unit of the type shown in FIG. 1, with the capsule being positioned in the basket 16 and below the open end of the bottle neck 15, it immediately absorbs a substantial quantity of water because of its porosity. The absorbed water being in intimate contact with the metallic silver dispersed in the capsule, causes the release of silver ion into the absorbed water, and silver ion from the absorbed water is thereby dispersed into the surrounding water. Within a relatively short period of time, the ion thereby released finds its way into the body of water within the bottle 14 and the container 10, with initial creation and subsequent maintenance of a silver ion concentration within the entire body of water which is capable of inhibiting the growth of bacteria and other microorganisms. In general, the silver ion concentration within the main body of water is maintained with a range of about 10 to 30 parts per billion (ppb), which is effective to control growth of any organisms present in a good quality drinking water, and to maintain such water safe in a dispensing unit.

While a capsule made as described above serves to maintain an effective level of silver ion in various types of water, it is considered to be particularly effective and desirable when used in connection with drinking water having not more than 150 ppm of dissolved solids. It has been observed that when the amount of dissolved solids in the water increases beyond 150 ppm, the effectiveness of the capsule in disinfecting the water appears to be impaired.

The capsule described above has a relatively long useful life. For the periods in which the capsule has been used under test conditions, no impairment in activity has been noted. Judged by such experimental use, it is considered that the useful life of a capsule is well over one year.

It is advisable to periodically clean a capsule to remove any surface deposits. Any such deposits can be readily removed without impairing the effectiveness of the capsule simply by washing off the surface with the aid of a brush.

An example of the invention is as follows:

EXAMPLE

The kaolin used was one sold under the trade name of Kaolex. 10% of bentonite was added to the kaolin. The resulting dry mix analyzed as specified above by way of example. An 8.5% silver nitrate solution was added to the mix to form a mass of moldable consistency. The mold was constructed to form a capsule shaped as in FIGS. 3 and 4. After molding, the molded body while within the mold was dried in a hot air oven over a period of 24 hours to eliminate substantially all of the moisture. The green clay body was then placed in a kiln and fired to a temperature of about 1900° F. The total firing cycle was 12 hours, including an initial period for heating from ambient to 1900° F., holding at that temperature for 2 hours, and then cooling for an additional 12 hours. The body of the capsule measured 2¾ inches maximum diameter and 1 inch in height, with ribs ¼ inch wide and projecting ⅛ inch from the body. The body at its perimeter (upper edge) was about 1/16 inch thick, and 9/16 inch thick at its central portion. The volume of the capsule was 60 ml (3.66 cu. inches) and the weight was 98 grams. When immersed in water, the water absorption was 24 ml. The amount of metallic silver was 2.0 grams, resulting from the reduction of 3.15 grams silver nitrate.

Tests were made to determine the effectiveness of the capsule in inhibiting bacterial growth. Fifty drinking water dispensers of varying types (12 of the hot/cold water type, 4 of the type provided with electrical coolers, and 9 of the simple olla type) were each equipped with a capsule made as described above. At regular intervals (once each 7 days) over a total test period of 45 days, samples were taken from the reservoir and faucet of each dispenser and were read at 24 hours and 5-7 days of incubation. It was found that the control of bacteria ranged from 96.1 to 98.7%, compared to bacteria present in the same types of dispensers operating without the capsule. The same test was carried out with a capsule of equal size and weight but containing 1 gram of silver. This gave bacteria control over a range of 92.7 to 96.3%.

The water used in both of the above tests was good quality drinking water having less than 150 ppm dissolved solids in the form of mineral salts.

What is claimed is:

1. In water dispensing apparatus, a container for storing water, a vessel below the container having an upper open end adapted to communicate with the lower open end of the container, means for dispensing water from the vessel, upwardly open basket means generally surrounding and extending below the lower open end of the container, the basket means having openings for flow of water from the interior of the same into the vessel, and a ceramic body disposed within the lower portion of the basket means below said lower open end of the container and immersed in the water within the vessel, said body being formed of porous ceramic material having metallic silver dispersed within the same and adapted to absorb water through its exterior surfaces and retain absorbed water in static condition within the body, said basket and said ceramic body being so disposed as to cause water to flow from the container downwardly toward and about the exterior surfaces of the body and through the openings in the basket when water is dispensed from the vessel, said ceramic body being provided with ribs on the lower side of the same which support the body on and spaced from the adjacent surface of the basket, and in which the central portion of the body has a hole extending through the same, said ribs serving to aid flow of water about the body.

* * * * *